US007226751B2

United States Patent
Erich et al.

(10) Patent No.: US 7,226,751 B2
(45) Date of Patent: Jun. 5, 2007

(54) DETECTING THE PRESENCE OF PYRUVATE KINASE ISOENZYME IN FECES

(75) Inventors: Eigenbrodt Erich, Linden (DE); Scheefers-Borchel Ursula, Wettenberg (DE); Scheefers Hans, Wettenberg (DE)

(73) Assignee: ScheBo Biotech AG, Giessen (DE)

( * ) Notice: Subject to any disclaimer, the term of this patent is extended or adjusted under 35 U.S.C. 154(b) by 566 days.

(21) Appl. No.: 10/102,755

(22) Filed: Mar. 22, 2002

(65) Prior Publication Data

US 2002/0102623 A1  Aug. 1, 2002

Related U.S. Application Data

(63) Continuation-in-part of application No. PCT/EP00/09303, filed on Sep. 22, 2000.

(30) Foreign Application Priority Data

Sep. 24, 1999 (DE) ................ 199 45 947

(51) Int. Cl.
*G01N 33/53* (2006.01)
(52) U.S. Cl. ............... 435/7.23; 435/7.1; 435/7.4; 435/7.23; 436/518
(58) Field of Classification Search ............ 435/7.4, 435/7.23, 7.1; 436/518
See application file for complete search history.

(56) References Cited

U.S. PATENT DOCUMENTS

| 4,012,285 | A | * | 3/1977 | Pfleiderer et al. | ............ 435/7.4 |
| 4,876,191 | A | * | 10/1989 | Hollander et al. | ........... 435/7.4 |
| 5,683,987 | A | * | 11/1997 | Smith | ......................... 514/44 |
| 5,972,628 | A | * | 10/1999 | Eigenbrodt et al. | ........ 435/7.23 |
| 6,258,541 | B1 | * | 7/2001 | Chapkin et al. | ............... 435/6 |

* cited by examiner

*Primary Examiner*—Christopher R. Tate
*Assistant Examiner*—Deborah A. Davis
(74) *Attorney, Agent, or Firm*—Rothwell, Figg, Ernst & Manbeck, P.C.

(57) ABSTRACT

In order to selectively, qualitatively or/and quantitatively detect the pyruvate kinase isoenzyme of the tumor M2-PK type (tumor M2-PK) which serves as a tumor marker in human and animal feces to detect a malignant process in the gastrointestinal tract, tumor M2-PK is detected in a stool specimen by an immunoassay technique with the aid of at least one antibody which specifically binds tumor M2-PK and does not cross-react with any other pyruvate kinase isoenzyme. A test kit for diagnosing malignant tumor growth in the gastrointestinal tract and in particular in the intestines contains at least one receptor for tumor M2-PK which does not cross-react with any other pyruvate kinase isoenzyme and optionally contains additional reagents that are necessary for carrying out an immunoassay.

17 Claims, No Drawings

DETECTING THE PRESENCE OF PYRUVATE KINASE ISOENZYME IN FECES

CROSS REFERENCE TO RELATED APPLICATION

This application is continuation-in-part of International Application PCT/EP00/09303, filed Sep. 22, 2000 and designating the U.S.

The present invention relates to a method for the detection of a malignant process in the gastrointestinal tract of humans or animals.

In particular, the present invention concerns a method for the selective, qualitative or/and quantitative detection of the pyruvate kinase isoenzyme of the type tumor M2 (tumor M2-PK) which serves as a tumor marker, in human and animal feces for detecting a malignant process in the gastrointestinal tract and the abdominal cavity (oesophagus, stomach, small intestine, pancreas and large intestine) and a test kit for carrying out the method.

Organ-specific isoenzymes which remain within a tumor during the metastasising process are excellent indicators for malignancy (tumor markers). Isoenzymes of carbohydrate metabolism, in particular pyruvate kinase isoenzymes and above all pyruvate kinase, in particular, of the type tumor M2-PK appear to be such indicators.

Pyruvate kinase (PK) isoenzymes (E.C.2.7.1.40) exist as four subtypes: L, R, M1 and M2. Investigations have shown that malignant tumors of human or animal origin express a particular type of pyruvate kinase of the M2 type, the so-called tumor M2-PK and indeed independent of their origin (Eigenbrodt et al., Critical Reviews in Oncogenesis, 3 (1, 2) (1992) 91–115).

All hitherto examined tumors contained this special isoenzyme. In contrast to other pyruvate kinases which are mainly present in a tetrameric form, tumor M2-PK occurs in a dimeric or monomeric form and its serine and tyrosine is phosphorylated by an oncogene-coded kinase (Eigenbrodt et al., (1997) Anticancer Research, 17:3153–3156, Eigenbrodt et al., (1998) Anticancer Research 18:3267–3274, Steinberg et al., (1999) virchows Arch 434: 213–220).

The conversion of the tetrameric form of the isoenzyme into the monomeric and/or dimeric form appears to be an important step in tumor formation. This special tumor M2-PK isoenzyme is released by the tumor cells and can be detected quantitatively in body fluids. The concentration of the tumor M2-PK isoenzyme correlates with the malignancy of the tumors. Hence tumor M2-PK can be regarded as a tumor marker.

Antibodies have already been developed which are specific for tumor M2-PK and do not cross-react with other pyruvate kinase isoenzymes of the L, R, M1 or M2 (normal M2) type. By means of these antibodies a sensitive immunoassay could be developed to detect tumor M2-PK in the sera or plasma of tumor patients (Scheefers-Borchel et al., (1994), Research-trends, R. Klapdor (ed.), W. Zuckschwerdt Verlag GmbH, Munich).

Up to now this qualitative and quantitative detection of pyruvate kinase of the type tumor M2 (tumor M2-PK) in serum or plasma has been carried out by means of an ELISA as described among others in EP 0 444 118.

This test has very good sensitivities and specificities in numerous tumor diseases (Brinck, U., Eigenbrodt, E., Oehmke, M., Mazurek, S., Fischer, G. (1994) L-and M2 pyruvate kinase Expression in Renal Cell Carcinomas and their Metastases, Virch. Arch., 424: 177–185; Cerwenka, H., Aigner, R., Bacher, H., Werkgartner, G., El-Shabrawi, A., Quehenberger, F., Mischinger, H. J. (1999) TUM2-PK (pyruvate kinase type tumor M2), CA19-9 and CEA in Patients with Benign, Malignant and Metastasizing Pancreatic Lesions, Anticancer Research 19: 849–852; Eigenbrodt, E., Mazurek, S., Friis, R. R. (1998) Double role of pyruvate kinase type M2 in the regulation of phosphometabolite pools, Cell growth and Oncogenesis 15; Hugo, F., Fischer, G., Eigenbrodt, E. (1999) Quantitative Detection of Tumor M2-PK in Serum and Plasma, Anticancer Research (1999), 19:2753–2758; Mazurek, S., Grimm, H., Wilker, S., Leib, S., Eigenbrodt, E. (1998) Metabolic Characteristics of Different Malignant Cancer Cell Lines, Anticancer Research 18: 3275–32821; Oremek, G. M., Eigenbrodt, E., Rädle, J., Zeuzem, St., Seiffert, U. B. (1997) Value of the Serum Levels of the Tumor Marker TuM2-PK in Pancreatic Cancer, Anticancer Research, 17: 3031–3034 Oremek, G. M., Teigelkamp, S., Kramer, W., Eigenbrodt E., Usadel, K.-H. (1999) The Pyruvate Kinase Isoenzyme Tumor M2 (Tumor M2-PK) as a Tumor Marker for Renal Carcinoma, Anticancer Research (1999), 19:2599–2602; Scheefers-Borchel, U., Scheefers, H., Michel, Will, A., Fischer, G., Basenau, D., Dahlmann, N., Laumen, R., Mazurek, S., Eigenbrodt E. (1994) Quantitative determination (ELISA) of pyruvate kinase type tumor M2, in: Current Tumor Diagnosis, Applications, Clinical Relevance, Research-trends. R. Klapdor (ed.), W. Zuckschwerdt Verlag GmbH, Munich; Wechsel, H. W., Petri, e., Feil G., Bichler, K.-H. (1997) Tumor Specific Pyruvate Kinase (tumor M2-PK): A potential marker for renal cell carcinoma (RCC)1, J. Urology 157:424; Wechsel, H. W., Petri, E., Bichler, K.-H., Feil G. (1999) Marker for Renal Cell Carcinoma (RCC): The Dimeric Form of Pyruvate Kinase Type M2 (tumor M2-PK), Anticancer Research (1999), 19: 2583–2590.

Tumor markers are defined and classified as follows:

Tumor markers are macromolecules or antigens occurring in the blood, serum or other body fluids whose concentration changes are related in a certain manner to the formation and growth of malignant tumors of an individual.

Criteria for Tumor Markers

The "ideal" tumor marker should have the following properties:
- high specificity i.e. not detectable in benign diseases and healthy persons;
- high sensitivity i.e. it can be detected in a high percentage of the tumor patients;
- organ specificity,
- good correlation to the tumor stages or the tumor mass;
- good informative value with regard to malignancy;
- correlation with the prognosis;
- reliable predictive values.

The criteria of 100% specificity and 100% sensitivity have not been hitherto fulfilled by any of the known tumor markers.

Since however, the tumor M2-PK can be detected in all tumor diseases in the serum or blood plasma of patients, it does not yield any information on the type and location of the affected organ or tissue in the body of the patient. Moreover, it would be desirable to be able to detect a tumorous process in the gastrointestinal tract as early as possible and especially in a growth phase in which the tumor has not yet made contact with the vascular system of the body (in the polyp cancer sequence, chronologically before the infiltration of the submucosa).

When a neoplastic process is suspected in the gastrointestinal tract especially with regard to the so-called adenoma carcinoma sequence of polyps (polyposis coli), various determination methods are used according to the prior art in an attempt to detect occult blood in the feces. Non-immunological tests (e.g. pseudoperoxidase activity, porphyrin test) and immunological tests are used for this purpose.

However, both types of test are not very specific since numerous influencing parameters can interfere with them (false positive/false negative) e.g. by patient non-adherence to absolutely necessary prescribed diets and by a number of drugs and by excessive vitamin C administration (e.g. in vegetables, fruit juices etc., Thomas, L., "Labor und Diagnose", 5$^{th}$ edition, 1998).

A positive test for occult blood in feces must be further investigated until the source of bleeding has been localized or the cause of bleeding has been found. The clinical finding justifies in any case further diagnostics which should be carried out as quickly as possible e.g. by endoscopy, sonography, X-ray. However, the presence of blood in feces is not always due to a tumorous process and conversely the absence of blood in feces not always reliably mean that no tumor is present in the intestine.

Hence the object of the invention is to satisfy the continuing need for a specific method which is easy to carry out and enables an especially early and unambiguous detection of a neoplastic process above all with regard to the problems associated with the so-called adenoma carcinoma sequence of polyps (polyposis coli) in the gastrointestinal tract.

This object is achieved according to the invention by a method for the detection of a malignant process in the gastrointestinal tract of humans or animals, which is characterized in that a pyruvate kinase isoenzyme which serves as a tumor marker or fragment thereof is determined in a stool specimen. Preferably, the pyruvate kinase isoenzyme or fragment thereof is determined immunochemically, e.g. by an anti-pyruvate kinase isoenzyme antibody or by a pyruvate kinase isoenzyme specific aptamer. In particular, the pyruvate kinase isoenzyme or fragment thereof is determined by an antibody which is a monoclonal or polyclonal antibody and which does not cross-react with other constituents of human or animal feces, e.g. other proteins.

In a preferred embodiment a sample is contacted with at least two different receptors, of which the first receptor $R^1$ is present in a solid phase and is capable of binding to a pyruvate kinase isoenzyme, and at least one second receptor $R^2$ is present in a liquid phase and is capable of binding to a pyruvate kinase isoenzyme and a receptor, wherein receptor $R^2$ carries a label or mediates binding to a detectable molecule, the solid phase is separated from from the liquid phase, the label or the detectable molecule is determined, wherein an antibody is used as at least one of the receptors $R^1$ or $R^2$ which specifically binds to said pyruvate kinase isoenzyme. Advantageously, an antibody which specifically binds to pyruvate kinase isoenzyme is used as first receptor $R^1$ bound to a solid phase, and a second antibody which binds to pyruvate kinase isoenzyme is used as soluble receptor $R^2$.

The invention further relates to a method for the detection of a pyruvate kinase isoenzyme, which is characterized in that at least one monoclonal or polyclonal antibody against a pyruvate kinase isoenzyme is used. For the detection the pyruvate kinase isoenzyme is preferably determined qualitatively or quantitatively in human or animal feces.

Particularly preferred, the invention relates to a method for the selective qualitative or/and quantitative detection of the pyruvate kinase isoenzyme of the type tumor M2 (tumor M2-PK) which serves as a tumor marker, in human and animal feces for detecting a malignant process in the gastrointestinal tract which is characterized in that the tumor M2-PK is determined in a stool specimen by an immunoassay technique with the aid of at least one antibody which specifically binds tumor M2-PK and does not cross-react with any other pyruvate kinase isoenzyme.

It was namely found that the content of tumor M2-PK can be directly detected in the feces of tumor patients, the content being directly proportional to the level of the malignant process in the gastrointestinal tract.

This is all the more surprising since extensive investigations of other specific proteins in the feces gave no indication that they could be used as tumor markers.

Surprisingly, the considerable proteolytic activity and the extreme physiological conditions (e.g. pH value, acidic in the stomach, alkaline in the intestine) of the gastrointestinal tract did not have a lasting adverse effect on the structure or the physicochemical properties of tumor M2-PK. This also applies to the detection of tumor M2-PK by immunological methods.

It was demonstrated by the invention that, despite the protein denaturation and protein digestion in the gastrointestinal tract described above, it is possible to carry out a specific test for tumor M2-PK in the feces of tumor patients. Up to now tumor M2-PK was only determined quantitatively in native, non-digested patient samples (body fluids, sera, blood plasma) and this determination was used in clinical tumor diagnostics for numerous tumor diseases.

However, it has now been surprisingly found that tumor M2-PK also remains quantitatively detectable in intensively homogenized stool specimens that have been stored for long periods (for example during sample shipment). A distinct reaction is obtained even when the stool is highly diluted.

Furthermore it was also surprisingly found that the test is selective in the stool specimen even without prior extraction. However, it is preferable to use an extraction method which preferably uses a special detergent (CHAPS) (the extraction method is described in more detail in example 2).

In a preferred embodiment of the invention a monoclonal antibody is used as the antibody which is obtainable from the hybridoma cell line clone 1 (deposited at the "Deutsche Sammlung für Mikroorganismen" under the number DSM ACC 2155), or an antibody is used which has the same specificity and selectivity. Such antibodies can for example be produced as described in EP 0 444 118. However, the production is uncritical since methods for the production of specific monoclonal antibodies are well-known to persons skilled in the art. For this purpose the antigen i.e. tumor M2-PK in the present case, is used in a form purified in the usual manner (or fragments of the same) to generate antibodies. In principle the method which was first described by Köhler and Milstein can be used for this, whereby a person skilled in the art also knows modifications and further developments of this method. The production is uncritical provided that specific antibodies are obtained which can be established by selection. Antibodies are selected which specifically bind tumor M2-PK but not one of the other isoenzymes of pyruvate kinase and also not the non-tumour M2-PK form.

In the method according to the invention the following steps are preferably carried out:

(a) The sample is contacted with at least two different receptors of which the first receptor is present in a solid phase and is capable of binding to tumor M2-PK and the second receptor R2 is present in a liquid phase and is also capable of binding to tumor M2-PK, wherein receptor R2 carries a label or mediates binding to a detectable molecule;

(b) the solid phase is separated from the liquid phase;

(c) the label or the detectable molecule in the solid phase is determined by known methods and thus the amount of tumor M2-PK present in the sample is quantified, wherein according to the invention an antibody is used as at least one of the receptors 1 or 2 which can specifically bind to tumor M2-PK and discriminates between other pyruvate kinase isoenzymes i.e. does not bind any of the other isoenzymes and also does not bind the non-tumor M2-PK form.

Although it is of course also possible to use two antibodies which are both capable of specifically binding to tumor M2-PK according to the above definition, it is usually sufficient to use a not so specific antibody for the second of the receptors 1 or 2. If an antibody that can only bind specifically to tumor M2-PK has already been used as receptor R1, only tumor M2-PK is present bound to this receptor after separating the liquid phase. Hence the detection receptor R2 must only be capable of binding to tumor M2-PK but does not necessarily have to allow a discrimination between PK isoenzymes.

If a less specific antibody is used as receptor R1, a receptor R2 is used which is capable of specifically binding only to tumor M2-PK such that a detectable signal is only generated when tumor M2-PK is present.

However, as already mentioned above two specific antibodies that can only bind to tumor M2-PK can also be used in order to possibly achieve an even higher specificity.

In a preferred embodiment of the method according to the invention an antibody that can specifically bind to tumor M2-PK and discriminates between other pyruvate kinase isoenzymes is used as the receptor R1.

In a further preferred embodiment an antibody which itself carries a label is used as receptor R2. This allows an even more rapid direct detection compared to the case in which a detectable molecule is bound to receptor R2. A further preferred embodiment of the invention is a method in which an enzyme-bound antibody is used as receptor R2 and the method is carried out as an Enzyme Linked Immuno Sorbent Assay (ELISA).

A further subject matter of the invention is a test kit for diagnosing malignant tumor growth in the gastrointestinal tract, which is characterized in that it contains at least one receptor for pyruvate kinase isoenzyme which does not cross-react with other stool proteins and optionally other reagents necessary for carrying out an immunoassay. Preferably, the test kit contains a pyruvate kinase isoenzyme antibody bound to a solid phase. A preferred embodiment is a test kit for diagnosing a malignant tumor process in the gastrointestinal tract and in particular in the intestine which contains at least one receptor for tumor M2-PK which does not cross-react with any other pyruvate kinase isoenzyme and optionally other reagents necessary for carrying out a monoassay.

The test kit is especially designed to carry out the method according to the invention. Hence the test kit preferably contains a second receptor R2 which carries a label or mediates binding to a detectable molecule.

An antibody which binds specifically to tumor M2-PK is preferably immobilized on a solid phase by means of known methods. In a preferred embodiment of the invention this solid phase is also a component of the test kit. The specimen to be examined is then contacted with the preferably dissolved protein and bound to the solid phase in a suitable buffer system by means of the antibodies. After washing the immobilized antibody-tumor-M2-PK complex obtained in this manner, a further labelled second antibody (e.g. carrying biotin) is then added which binds to another epitope of tumor M2-PK. Then the label is determined e.g. with the aid of streptavidin-peroxidase. The amount of bound marker is directly proportional to the amount of tumor M2-PK in the specimen. It is expedient for the test kit to contain reference material with a known content of tumor M2-PK for quantitative determination.

Of course all other types of immunological detection methods that can be carried out with the aid of antibodies can also be used according to the invention. A person skilled in the art knows many alternatives especially for the test kit formulation which are all in principle suitable for carrying out the method according to the invention. Thus for example a test can also be designed in the form of a test strip on which the required antibodies are arranged in different zones of the test strip either in a soluble form or solid phase-fixed. The specimen or the liquid fraction of the specimen or an extract can then migrate through the test strip and generate a signal at the detection site when tumor M2-PK is present in the specimen. The exact arrangement of the individual components of the test strip depends on the immunological method that is used and can easily be realised by a person skilled in the art.

Within the scope of the present invention the term "receptor" or "antibody" also encompasses parts or fragments of receptors or antibodies which still mediate the necessary binding to tumor M2-PK. In this connection it is also possible to use a conjugate of two antibodies instead of a single antibody. For example one can envisage using an antibody capable of binding to tumor M2-PK as receptor R2 and to use another labelled antibody for the detection which is directed towards the Fc part of receptor 2 and carries a label or which is in turn coupled to a detectable molecule. This conjugate formation from two antibodies should also be encompassed within the scope of the present invention when R2 is defined such that it mediates binding to a detectable molecule. This applies analogously to the binding of receptor R1 to the solid phase. This binding can also be achieved by means of solid phase-coupled antibodies to which the Fc part of receptor R1 binds.

Many other embodiments of the invention are conceivable and easy to carry out by a person skilled in the art. Hence these embodiments are also encompassed within the scope of the present invention provided they enable the detection of tumor M2-PK in a stool specimen.

In particularly preferred embodiments of the invention the test kit contains the monoclonal antibody which is obtainable from the hybridoma cell line clone 1 (DSM ACC 2155) as one of the receptors. In a further preferred embodiment a solid phase-bound antibody specific for tumor M2-PK is used which does not cross-react with other isoenzymes or with the non-tumour M2-PK.

The soluble receptor R2 is preferably a labelled antibody.

The determination of the tumor marker pyruvate kinase isoenzyme can also be performed with other, in particular, with commercially available immunochemical test systems.

According to the invention it is also possible to determine the analyte concentration by means of biosensors such as amperometric sensors, potentiometric, ion-selective potentiometric or photometric sensors or those employing semiconductor electrodes such as field effect transistors (FET), chemosensitive field effect transistors (CHEMFET), suspended-gate field effect transistors (SGFET) or ion-sensitive field effect transistors. Such biosensors are summarized in E. A. H. Hall and G. Hummel in "Biosensoren", Springer Verlag Heidelberg, Germany, 1995. Further developments of ion-sensitive field effect transistors (ISFET) or optical detectors are described among others by F. Aberl and H. Wolf in "Aktuelle Trends in der Immunsensorik", Labor 2000, p. 70–96 (1993). The method according to the invention is also suitable for procedures using piezoelectric oscillating quartz crystals and surface wave elements that can be used as microbalances. In this case the primary antibody (the so-called catcher) is immobilized on a piezoelectric substrate and a change in the oscillating frequency of the quartz crystal is measured after binding to the pyruvate kinase isoenzyme of the type tumor M2-PK to be analysed. Such sensors are described for example by A. Leidl et al., in "Proceedings of the Second International Symposium on Miniaturized Total Analyses Systems µTAS", Basle, 1996. Quartz crystal microbalances as described by C. Köslinger et al., Fresenius J. Anal. Chem (1994), 349: 349–354 have proven to be particularly suitable or Kandelaber technology, e.g. from IBM, Inc. can be used.

According to the invention it is also possible to determine the analyte concentration using immunochromatographic methods such as so-called visual rapid tests or lateral flow tests.

The sensitivity and test kinetics of the immunoassay and other aspects such as dynamic range and format flexibility can be significantly improved by using electro-chemiluminescence. Electrochemiluminescence is the process by which light is generated when a low voltage is applied to an electrode through which a cyclic redox reaction in a ruthenium metal ion is triggered (Bruno, G. (1997) Rec. Rp pp. 175–179; Williams R. (1996), Amer. Biotech., p. 26). A similar technology which is also suitable is the TRACE technology from CIS company, Germany.

The antibodies to be used according to the invention are obtainable in a known manner as described above. Preferably tumor M2-PK is firstly isolated for example from tumors of the large intestine (by chromatography on DEAE Sephadex A-50 and subsequent affinity chromatography on a blue Sepharose CL 6B) as described by K. Scheiner-Bobis (Doctoral thesis of the Justus-Liebig University Gießen, submitted on 8$^{th}$ Nov. 1988). Afterwards an experimental animal is immunized with the tumor M2-PK obtained in this manner or with fragments thereof which have the appropriate epitopes and the antibodies that are formed are isolated. Such fragments which are used for immunization can for example be derived from a protease digestion of the purified tumor M2-PK or be composed of synthetic partial peptides of the same. The preparation of such partial peptides is known to a person skilled in the art. In this procedure sequences that may contain the appropriate epitopes are selected from the sequence for example with the aid of computer programs.

It is then tested whether these sequences can be utilized to produce specific antibodies.

Monoclonal antibodies obtainable by the method of Köhler, Milstein (Nature 256, 495–497 (1975) are preferably used. In this method BALB/C mice are for example immunized with isolated tumor M2-PK and the spleen cells of these animals are fused with a myeloma cell line for such as PA 1. The antibodies secreted in the ascites are tested for their specificity for example in an ELISA or RIA and isolated. The antibodies obtained in this manner usually belong to the IgG1 class.

A further subject matter of the present invention is a monoclonal antibody which specifically binds to a pyruvate kinase isoenzyme. Particularly preferred is a monoclonal antibody which specifically binds to the pyruvate kinase isoenzyme of type tumor M2 and does not cross-react with any other pyruvate kinase isoenzyme.

The antibodies according to the invention are obtainable by basically known methods. For example, the pyruvate kinase isoenzyme is first isolated and purified, if necessary. Thereafter, a test animal can be immunized with the thus obtained pyruvate kinase isoenzyme and fragments thereof, respectively, having the corresponding epitopes, and the antibodies formed can be isolated. Fragments used for immunization, for example, can consist of a protease digestion of a purified pyruvate kinase isoenzyme or of synthetic partial peptides thereof. The production of such partial peptides is known to the skilled artisan. Thereby, partial sequences containing corresponding epitopes can be selected from the total sequence, e.g. by means of computer programs. These sequences are then tested for their usefulness for the production of specific antibodies.

Preferably, the monoclonal antibodies of the invention are produced according to the Koehler, Milstein method (Nature 256, 495–497 (1975)). According to this, for example, BALB/c mice are immunized with isolated PGDS and the spleen cells of these animals are fused with a myeloma cell line, e.g. PA 1. The secreted antibodies are tested for their specificity, e.g. in ELISA or RIA, and isolated.

The present invention further relates to aptamers binding specifically to a pyruvate kinase isoenzyme. Particularly preferred are aptamers which specifically bind to pyruvate kinase isoenzyme of type tumor M2 and do not cross-react with any other pyruvate kinase isoenzyme. Aptamers are oligonucleotide sequences having specific binding properties. The aptamers of the invention, for example, can be produced and identified, respectively, according to the methods described in U.S. Pat. No. 5,270,163 or Sumedha, Clin. Chem. 45 (1999) 1628–1650.

The invention is further elucidated by the following examples:

EXAMPLE 1

Weighing the Stool Specimens

A disposable tube of about 12 ml volume and a microbiological inoculating loop (e.g. Sarstedt) are tared out to zero with a sensitive digital laboratory balance. Subsequently the stool is weighed in with the inoculating loop by inserting the loop in the stool specimen and transferring the quantity of stool remaining on the tip (about 100 mg) into the disposable tube. A toothpick can be used instead of the inoculating loop.

The volumes of the extraction buffer to be added are varied according to the weighed mass of the stool specimens (e.g. 100 mg stool+10 ml buffer or 75 mg stool+7.5 ml buffer). Final concentration: 10 mg stool/ml extraction buffer.

EXAMPLE 2

Homogenization and Extraction of the Stool Specimens

The stool specimen suspension is mixed vigorously several times at room temperature with a test-tube shaking apparatus (e.g. VORTEX). The stools must be well homogenized. In order to ensure a complete extraction it is important to add the detergent CHAPS (3-[(3-cholamidopropyl) dimethyl ammonio]-1-propane sulfonate, 10 mM (Sigma) to the phosphate-buffered extraction buffer.

EXAMPLE 3

ELISA

An ELISA plate is coated with a monoclonal antibody which only recognizes tumor M2-PK. Tumor M2-PK from EDTA plasma samples and from standards binds to this antibody and is thus bound to the plate. A second monoclonal antibody which is biotinylated binds in the next incubation step to tumor M2-PK. Afterwards a conjugate of POD (peroxidase) and streptavidin is bound to the biotin unit of the antibody. The peroxidase oxidizes ABTS (2,2'-azino-bis-(3-ethyl-benzothiazoline-6-sulfonic acid) diammonium salt) to form a dark green colour. Finally the concentration of oxidized ABTS is determined photometrically.

EXAMPLE 4

Stool specimens are advantageously taken using the stool dosing system Quick-Prep from ScheBo Biotech AG, Germany.

The invention claimed is:

1. A method for the detection of a malignant process in the gastrointestinal tract of a human or animal, comprising
    obtaining a stool specimen, and
    detecting any pyruvate kinase isoenzyme of the tumor M2-PK type in said stool specimen as an indication of a malignant process in the gastrointestinal tract of said human or animal.

2. The method according to claim 1, wherein the pyruvate kinase isoenzyme of the tumor M2-PK type is detected immunochemically by contacting said stool specimen with at least one receptor which binds to a pyruvate kinase isoenzyme of the tumor M2-PK type and detecting any receptor bound to pyruvate kinase isoenzyme of the tumor M2-PK type.

3. The method according to claim 1, wherein said receptor is an anti-pyruvate kinase isoenzyme antibody.

4. The method according to claim 1, wherein said receptor is a pyruvate kinase isoenzyme specific aptamer.

5. The method according to claim 1, wherein said receptor is a monoclonal or polyclonal antibody which does not cross-react with constituents of human or animal feces other than pyruvate kinase isoenzyme of the tumor M2-PK type.

6. The method according to claim 1, wherein said stool specimen is contacted with at least two different receptors, wherein a first receptor $R^1$ is present in a solid phase and binds to a pyruvate kinase isoenzyme of the tumor M2-PK type, and at least one second receptor $R^2$ is present in a liquid phase and binds to a pyruvate kinase isoenzyme of the tumor M2-PK type and carries a label or mediates binding to a detectable molecule,
    further comprising separating said solid phase from said liquid phase, and
    determining any label or detectable molecule.

7. The method according to claim 6, wherein at least one of said receptors is an antibody.

8. The method as claimed in claim 7, wherein an antibody which specifically binds to pyruvate kinase isoenzyme of the tumor M2-PK type is used as first receptor $R^1$ bound to a solid phase, and a second antibody which binds to pyruvate kinase isoenzyme of the tumor M2-PK type is used as soluble receptor $R^2$.

9. The method according to claim 1, wherein said pyruvate kinase isoenzyme of the tumor M2-PK type is detected using ELISA, oscillating quartz crystals, microbalance, lateral flow, candelaber, TRACE or electrochemoluminescence technology.

10. The method according to claim 1, wherein at least one antibody which specifically binds pyruvate kinase isoenzyme of the tumor M2-PK type and does not cross-react with any other pyruvate kinase isoenzyme is used in an immunoassay technique for said detection.

11. The method as claimed in claim 7, wherein said antibody is a monoclonal antibody which is obtainable from the hybridoma cell line clone 1 (No. DSM ACC 2155), or an antibody which has the same specificity and selectivity.

12. The method as claimed in claim 6, further comprising quantifying the amount of pyruvate kinase isoenzyme of the tumor M2-PK type present in the sample, wherein receptor $R^2$ carries a label or mediates binding to a detectable molecule, the label or the detectable molecule in the solid phase is determined, and wherein at least one of the receptors $R^1$ or $R^2$ is an antibody which can specifically bind to pyruvate kinase isoenzyme of the tumor M2-PK type and discriminate between other pyruvate kinase isoenzymes.

13. The method as claimed in claim 12, wherein receptor $R^1$ is an antibody which specifically binds to pyruvate kinase isoenzyme of the tumor M2-PK type and discriminates between other pyruvate kinase isoenzymes.

14. The method as claimed in claim 13, wherein receptor $R^2$ is an antibody which carries a label.

15. The method as claimed in claim 13, wherein receptor $R^2$ is an enzyme-bound antibody and the method is carried out as an ELISA.

16. The method according to claim 6, wherein said pyruvate kinase isoenzyme of the tumor M2-PK type is detected selectively, quantitatively or qualitatively as an indication of said malignant process.

17. A method for the qualitative and/or quantitative detection of tumor M2-PK pyruvate kinase isoenzyme as an indication of the presence of a malignant process, comprising
    obtaining a test kit comprising at least one receptor for tumor M2-PK pyruvate kinase isoenzyme which does not cross-react with any other pyruvate kinase isoenzyme,
    obtaining a stool specimen,
    contacting said stool specimen with said at least one receptor for tumor M2-PK pyruvate kinase isoenzyme, and
    detecting any tumor M2-PK pyruvate kinase isoenzyme bound to said receptor, in said stool specimen as an indication of a malignant process.

* * * * *

UNITED STATES PATENT AND TRADEMARK OFFICE
CERTIFICATE OF CORRECTION

PATENT NO. : 7,226,751 B2 Page 1 of 1
APPLICATION NO. : 10/102755
DATED : June 5, 2007
INVENTOR(S) : Erich Eigenbrodt et al.

It is certified that error appears in the above-identified patent and that said Letters Patent is hereby corrected as shown below:

Title page should read,
Item --(75) Inventors: Erich EIGENBRODT
Ursula SCHEEFERS-BORCHEL
Hans SCHEEFERS--

Signed and Sealed this

Thirteenth Day of May, 2008

JON W. DUDAS
*Director of the United States Patent and Trademark Office*